(12) United States Patent
Tai et al.

(10) Patent No.: US 10,416,050 B2
(45) Date of Patent: Sep. 17, 2019

(54) LIQUID SAMPLE DRYING APPARATUS, DRIED SAMPLE TEST PIECE AND PREPARATION METHOD THEREOF

(71) Applicant: BIO MATERIALS ANALYSIS TECHNOLOGY CO., LTD., Hsinchu County (TW)

(72) Inventors: Lin-Ai Tai, Hsinchu County (TW); Yu-Ching Chen, Miaoli County (TW); Chih-Jung Sun, Kaohsiung (TW); Pin Chang, Hsinchu (TW)

(73) Assignee: Materials Analysis Technology, Inc., Zhubei, Hsinchu County (TW)

( * ) Notice: Subject to any disclaimer, the term of this patent is extended or adjusted under 35 U.S.C. 154(b) by 389 days.

(21) Appl. No.: 15/510,253

(22) PCT Filed: Sep. 10, 2014

(86) PCT No.: PCT/CN2014/086216
§ 371 (c)(1),
(2) Date: Mar. 10, 2017

(87) PCT Pub. No.: WO2016/037328
PCT Pub. Date: Mar. 17, 2016

(65) Prior Publication Data
US 2017/0307484 A1    Oct. 26, 2017

(51) Int. Cl.
*G01N 1/28* (2006.01)
*G01N 1/44* (2006.01)
*G01N 1/40* (2006.01)

(52) U.S. Cl.
CPC .............. *G01N 1/28* (2013.01); *G01N 1/44* (2013.01); *G01N 2001/4027* (2013.01)

(58) Field of Classification Search
CPC ..... G01N 1/28; G01N 1/44; G01N 2001/4027
See application file for complete search history.

(56) References Cited

U.S. PATENT DOCUMENTS

2010/0193398 A1* 8/2010 Marsh ................. G02B 21/34
206/710
2014/0007709 A1* 1/2014 Hsieh ...................... B01L 3/508
73/863.21

\* cited by examiner

*Primary Examiner* — Dennis White
(74) *Attorney, Agent, or Firm* — Rosenberg, Klein & Lee

(57) ABSTRACT

A liquid sample drying device, dried sample test piece and the preparation method for the dried sample test piece are provided. The liquid sample drying device includes two substrates, at least one spacer and a clamping member. Each of the two substrates includes a surface. The two surfaces face each other. The at least one spacer is located in between the substrates so as to form a sample region between the surfaces for receiving a liquid sample. The clamping member touches the two substrates so as to temporarily clamp and fix the two substrates and the at least one spacer together.

19 Claims, 22 Drawing Sheets

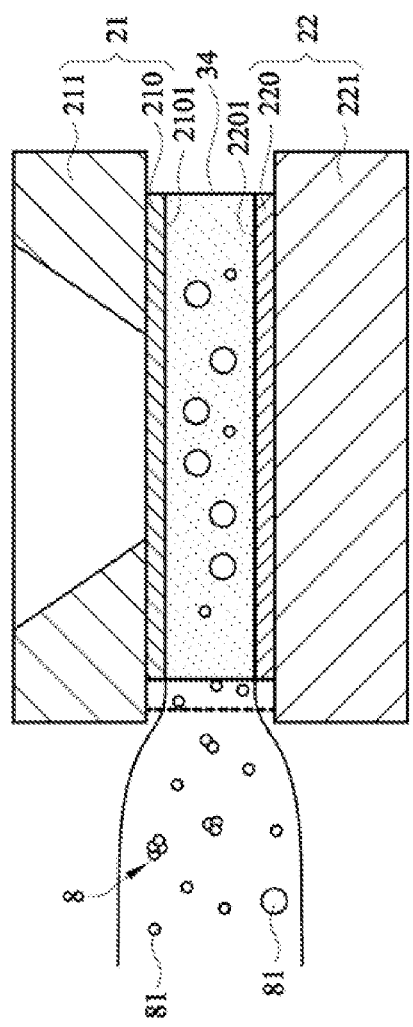

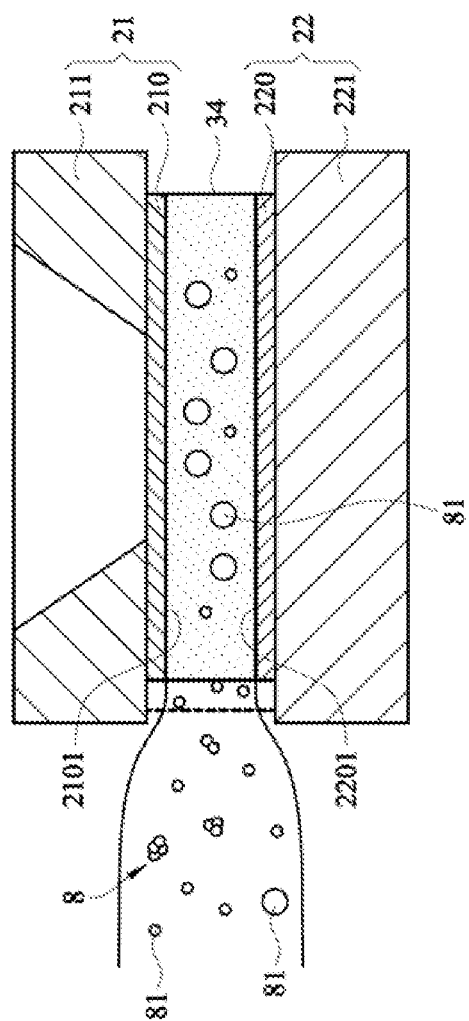

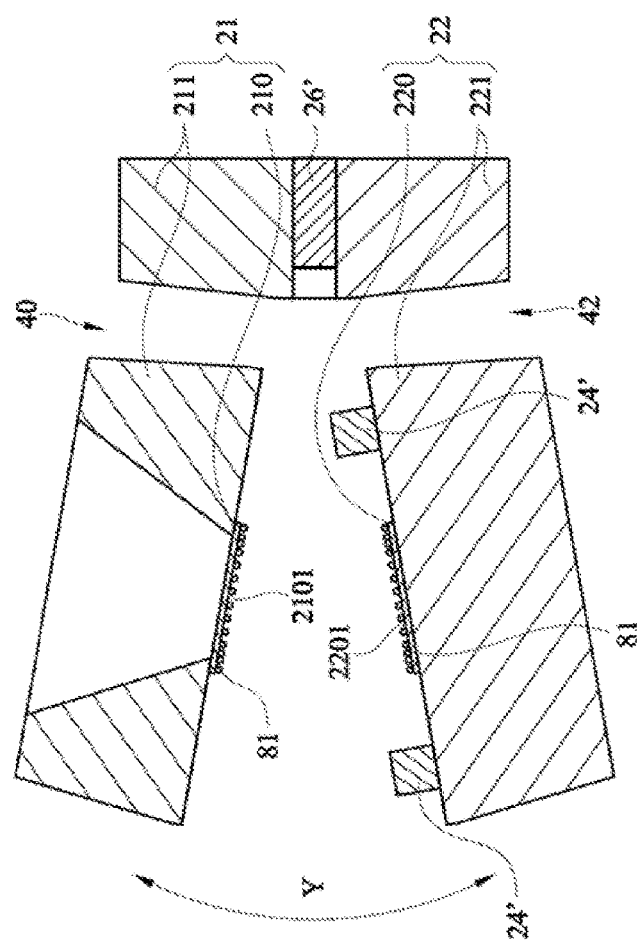

LIQUID SAMPLE DRYING APPARATUS, DRIED SAMPLE TEST PIECE AND PREPARATION METHOD THEREOF

BACKGROUND

Technical Field

The present invention relates to a liquid sample drying apparatus, and in particular, to a liquid sample drying apparatus, dried sample test piece and the preparation method thereof, wherein the dried sample test piece is suitable for observation under a microscope.

Related Art

Nowadays, a plurality types of microscopes have been developed, such as Optical Microscope, Atomic Force Microscope (AFM), Transmission Electron Microscope (TEM), Scanning Electron Microscope (SEM), etc.

In general, the sample test piece (hereinafter named by specimen) accommodated to each microscope should be developed accordingly, such as liquid sample specimen or dried sample specimen.

Referring to FIGS. 1A-1E, there are shown steps for preparing a dried sample specimen according to the prior art. A drop of liquid sample comprising suspended particulates 11C and 11N is placed on a substrate 10, as shown in FIGS. 1A and 1B. And then, dry the liquid sample 11. Because of the surface tension of the liquid, the suspended particulates 11C and 11N are dragged by unbalanced force and undergo an aggregation process during drying, as shown in FIGS. 1C-1E. The suspended particulates 11N in a part of the liquid sample 13 in FIG. 1C become the group of aggregation A1 in FIGS. 1D and 1E after drying. The observer cannot tell the aggregation is formed because of the property of the sample or the aggregation process during drying.

Therefore, it is a subject in need to be solved in the field on how to eliminate the aggregation caused by the surface tension during drying.

The US patent application No. 2014/0007709 A1 disclosed a sample drying device and a method thereof. The sample drying device comprises a top substrate and a bottom substrate. The top substrate and the bottom substrate are tightly bonded, that observation apparatuses cannot touch the surface of the substrate where the sample is dried. Consequently, the drying device is adapted for specific microscope, such as transmission electron microscope. However, the drying device and the dried sample kit are not adapted for microscopes that are operated by using probe(s) to approach the dried sample (to nanometer proximity), such as atomic force microscopes.

Therefore, it is a subject for the present invention to provide a sample drying apparatus, a dried sample specimen and a preparation method thereof that eliminate the aggregation caused by the surface tension and are adapted for a plurality types of microscopes.

SUMMARY

An objective of the present invention is to provide a sample drying apparatus and a preparation method thereof to obtain a dried sample specimen that eliminates the aggregation caused by the surface tension during drying. Furthermore, the sample drying apparatus is configured to be easy to be opened to form sample specimen with the dried sample exposed. The sample specimen of the present invention is adapted for a plurality types of microscopes and analysis methods, such as an electron microscope, an atomic force microscope, Matrix-Assisted Laser Desorption/Ionization Time of Flight Mass Spectrometry (MALDI-TOF-MS), probe contact electrical analysis, etc.

The present invention provides a liquid sample drying apparatus, comprising: two substrates, wherein each of the two substrates has a surface respectively and the two surfaces face each other; at least one spacer disposed between the two substrates so as to form a sample region between the two surfaces to receive a liquid sample; and a clamping member contacting the two substrates to temporarily fixing the two substrates and the at least one spacer.

According to the abovementioned liquid sample drying apparatus and the variations thereof, the present invention provides a preparation method for a dried sample specimen, comprising: providing the above mentioned liquid sample drying apparatus or the variation thereof; receiving a liquid sample to the sample region; drying the liquid sample, wherein a part of the dried liquid sample is attached to the surface of at least one of the two substrates and forms a dried sample specimen; and removing the clamping member to separate the dried sample specimen.

In an embodiment of the present invention, the step of removing the clamping member further comprises: cutting the two substrates to separate the dried sample specimen.

According to the abovementioned preparation method, the present invention provides a dried sample specimen prepared by the abovementioned preparation method, comprising: the part of the dried liquid sample and the substrate, wherein the part of the dried liquid sample is attached to the surface of the substrate. For example, a part of the dried liquid sample is attached to the first surface of the first substrate, the other part of the dried liquid sample is attached to the second surface of the second substrate.

The present invention further provides a liquid sample drying apparatus, comprising: two substrates, wherein each of the two substrates has a surface respectively and the two surfaces face each other; and at least one bonding member disposed between and bonding with the two substrates so as to form a sample region between the two surfaces to receive a liquid sample; wherein the substrates comprise at least one cutting region disposed between the sample region and the bonding region and extended in a direction of a thickness of the substrates.

In an embodiment of the present invention, the liquid sample drying apparatus further comprises at least one spacer disposed between the two substrates, wherein the at least one spacer and the sample region are on the same side of the cutting region to prevent the two surfaces from contacting each other to protect the dried sample.

According to the abovementioned liquid sample drying apparatus and the variations thereof, the present invention provides a preparation method for a dried sample specimen, comprising: providing the abovementioned liquid sample drying apparatus or the variation thereof; receiving a liquid sample to the sample region; drying the liquid sample, wherein a part of the dried liquid sample is attached to the surface of one of the two substrates and forms a dried sample specimen; and breaking the substrates along the cutting region to remove the bonding member and separate the dried sample specimen.

According to the abovementioned preparation method, the present invention further provides a dried sample specimen comprising: the part of the dried liquid sample and the substrate, wherein the part of the dried liquid sample is attached to the surface of the substrate. For example, a part of the dried liquid sample is attached to the second surface of the second substrate or the first surface of the first substrate.

The present invention further provides a liquid sample drying apparatus, comprising: two substrates, wherein each of the two substrates has a surface respectively and the two surfaces face each other; at least one bonding member disposed between and bonding with the two substrates so as to form a sample region between the two surfaces to receive a liquid sample; and at least one spacer disposed between the two substrates.

In an embodiment of the present invention, the spacer and the sample region are on the same side of the bonding member.

In an embodiment of the present invention, the first and second substrates comprise at least one first and second cutting regions respectively disposed between the sample region and the bonding region and extended in a direction of a thickness of the substrates.

According to the abovementioned liquid sample drying apparatus and the variations thereof, the present invention further provides a preparation method for a dried sample specimen, comprising: providing the abovementioned liquid sample drying apparatus or the variation thereof receiving a liquid sample to the sample region; drying the liquid sample, wherein a part of the dried liquid sample is attached to the surface of at least one of the two substrates and forms a dried sample specimen; and removing the at least one bonding member to separate the dried sample specimen.

In an embodiment of the present invention, the method of removing the at least one bonding member is selectively one of pressure applying, laser cutting, cutter wheel cutting, grinding, laser stealth dicing cutting or the combination thereof.

In an embodiment of the present invention, the method of drying the liquid sample is selectively one of natural evaporation, vacuum drying, low-humidity environment drying, heating drying, low-temperature drying, nitrogen environment drying, noble gas environment drying or the combination thereof.

According to the abovementioned preparation method for a dried sample specimen, the present invention further provides a dried sample specimen comprising: the part of the dried liquid sample and the substrate, wherein the part of the dried liquid sample is attached to the surface of the substrate.

In an embodiment of the present invention, a recess is disposed on the second substrate; the second surface is the bottom surface of the recess; the spacer is a side wall of the recess; and the sample region is in the recess.

In an embodiment of the present invention, the at least one spacer is fixed on one of the first and second substrates.

In an embodiment of the present invention, a recess is disposed on the second substrate; the second surface is the bottom surface of the recess; the at least one spacer is disposed beside the recess.

In an embodiment of the present invention, the recess can also be disposed on the first substrate. On the other hand, both the first and second substrates can comprise recesses. If the recesses face each other, the height of the sample region is the sum of the depths of the recesses.

In an embodiment of the present invention, the height of the sample region is between 0.1 µm and 10 µm.

In an embodiment of the present invention, an observation window is disposed on a substrate. For example, a first observation window is disposed on the first substrate; a second observation window is disposed on the second substrate; or the first and second observation windows are disposed on the first and the second substrates respectively. In one embodiment of the present invention, the first and second observation windows are opposite to each other.

BRIEF DESCRIPTION OF THE DRAWINGS

The disclosure will become more fully understood from the detailed description given herein below for illustration only, and thus are not limitative of the disclosure, and wherein:

FIG. 3A to FIG. 3C are sectional schematic diagrams showing steps of a preparation method for a dried sample specimen by using the liquid sample drying apparatus of the first embodiment in accordance with the present invention.

FIG. 6A to FIG. 6D are sectional schematic diagrams showing steps of a preparation method for a dried sample specimen by using the liquid sample drying apparatus of the third embodiment in accordance with the present invention.

DETAILED DESCRIPTION

For better description and understanding, the invention is described by embodiments incorporated with the attached figures. Elements or devices with the same number comprise the same or similar configurations or functions. The shapes, sizes and scales of the elements in the figures are only demonstrations, and should not be treated as the limitations of the present invention. Furthermore, an embodiment of the description may comprise a plurality of technical features, that does not mean that all technical features of the embodiment must be embodied at once. The liquid sample drying apparatuses of the present invention can be mass-produced by conventional semiconductor engineering and/or microelectromechanical system (MEMS) technique. The substrate is, for example, a first substrate 21 or a second substrate 22. The surface is, for example, a first surface 2101 or a second surface 2201. The observation window is, for example, a first observation window 30 or a second observation window 32.

Figure 1A:
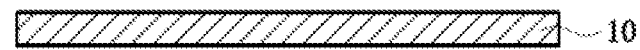
FIG. 1A to FIG. 1E are schematic diagrams showing steps of a conventional preparation method for a dried sample specimen.
Figure 1B:
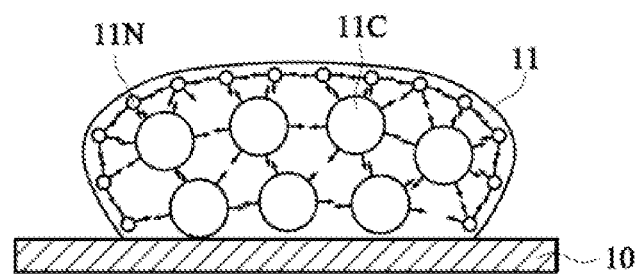
Figure 1C:
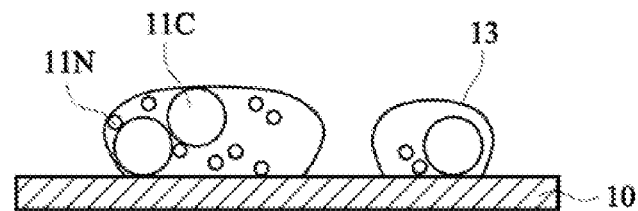
Figure 1D:
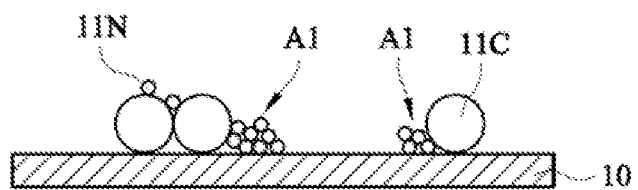
Figure 1E:
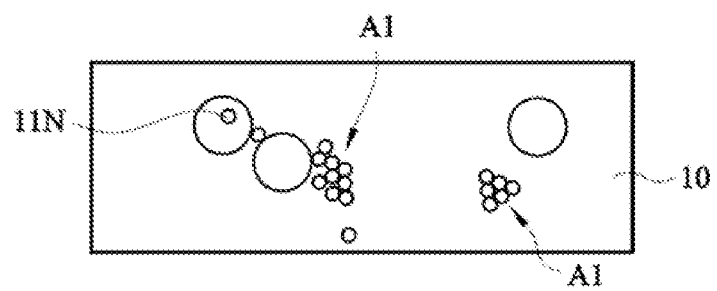
Figure 2A:
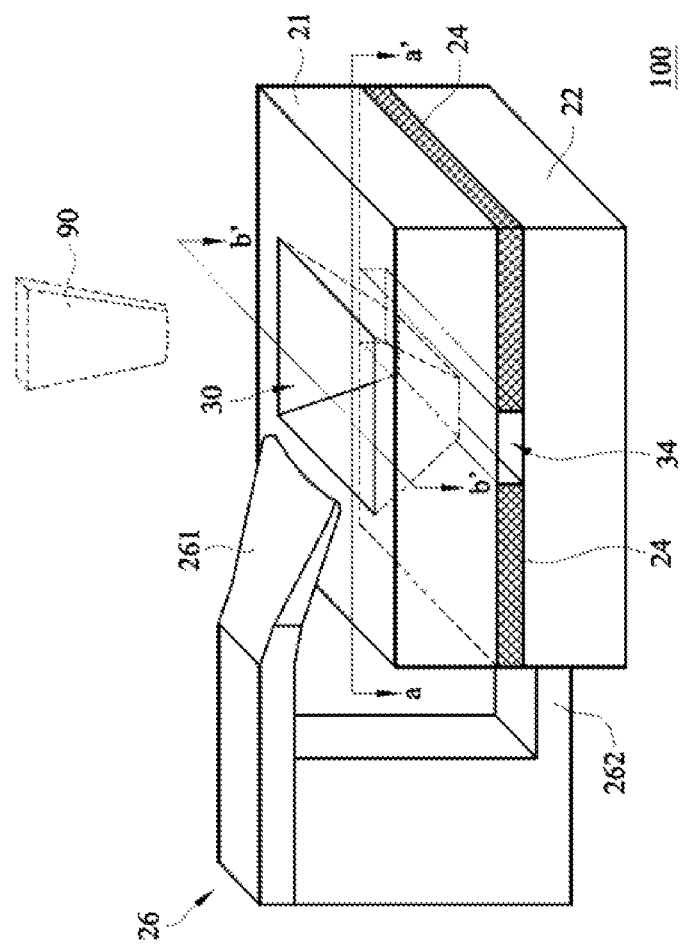
FIG. 2A is a schematic diagram of a liquid sample drying apparatus in accordance with a first embodiment of the present invention.
Figure 2B:
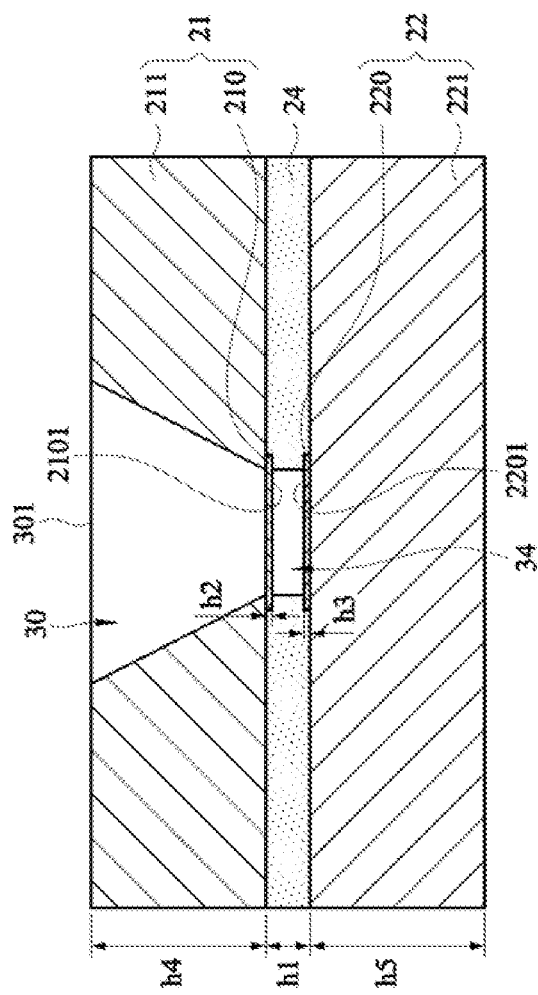
FIG. 2B is a sectional view of the liquid sample drying apparatus in accordance with the embodiment shown in FIG. 2A.

Referring to FIG. 2A and FIG. 2B, there are shown respectively a schematic structural diagram and a sectional view of a liquid sample drying apparatus in accordance with a first embodiment of the present invention. The liquid sample drying apparatus 100 comprises a first substrate 21, a second substrate 22, at least one spacer and a removable clamping member 26.

The first substrate 21 has a first surface 2101. In the present embodiment, the first substrate 21 has a first film 210 and a first base 211. The first film 210 is deposited on the first base 211. The surface of the first film 210 is the first surface 2101. A first observation window 30 is disposed on the surface of the first base 211 of the first substrate 21 opposite to the first film 210.

In particular, the bottom area of the opening 301 of the first observation window 30 is about 1 $\mu m^2$ to 1 $mm^2$. The first observation window 30 can be made by lithography and etching technique, a mask with predetermined pattern is firstly provided on the first base 211, and then an etching process is applied to the first base 211 to obtain the first observation window 30. The etching process is selectively one of an anisotropic wet etching process with potassium hydroxide etchant or a dry etching process with plasma.

In the present embodiment, the first film 210 is deposited on the first base 211 by selectively one of a chemical vapor deposition process, an acid washing process, a surface material deposition process or a polymer deposition process. The chemical vapor deposition process can be a plasma enhanced chemical vapor deposition (PECVD) process.

The first film 210 is made of one of silicon, silicon nitride, silicon oxide, silicon dioxide, silicon oxynitride, carbon, diamond film, graphene, silicon carbide, aluminum oxide, titanium nitride, titanium oxide, carbon nitride or the combination thereof. Furthermore, the first film 210 should be penetrable for electron beam. The thickness h2 of the first film 210 in the present embodiment is 2-200 nm, and is adapted for transmission electron microscope. The aforementioned technique is based on silicon wafer technology, the technique of the present invention is also adapted for other materials, where the strength, compactness, transmittancy and electron transmittance of the film, the conformity of the film and the substrate, the residual stress and surface property should be considered.

The first film 210 (first surface 2101) may be hydrophilic or hydrophobic. If the first film 210 is hydrophilic, the absorbability for polar liquid sample is enhanced. If the first film 210 is hydrophobic, the absorbability for nonpolar liquid sample is enhanced. The surface property of the film can be modified by physical modification, such as UV ozone modification or plasma modification, or chemical modification, such as acid washing, etching, anodizing, functional group adding, etc. In other embodiment of the present invention, the first surface 2101 may be the surface of the base.

The first base 211 is made of semiconductor material, such as single- or double-side polishing single crystalline silicon or metal oxide material, such as aluminum oxide. The thickness h4 of the first base 211 may be 0.2-0.8 mm for transmission electron microscope.

The second substrate 22 has a second surface 2201 facing the first surface 2101. In particular, the second substrate 22 of the present embodiment has a second film 220 and a second base 221. The material, design, preparation method and thicknesses h3 and h5 are the same as or similar to the first film 210 and the first base 211. Furthermore, the surface of the second film 220 is the second surface 2201 and is substantially parallel to the first surface 2101.

The liquid sample drying apparatus 100 comprises at least one spacer 24, and there are two spacers 24 in the present embodiment. The at least one spacer 24 is disposed between the first substrate 21 and the second substrate 22. A sample region 34 is formed among the first surface 2101, the second surface 2201 and the at least one spacer 24 for containing a liquid sample 8 (as shown in FIG. 3A). In particular, the spacer 24 of the present embodiment is non adhesive, such as silicon oxide or silicon, and is independently disposed on one of the first substrate 21 or the second substrate 22. In other embodiment of the present invention, the spacer 24 may be metal, ceramic or polymeric micrometer/nanometer scale particles, balls or cylinders. The height h1 of the spacer 24 is 0.1-20 µm or preferably 0.1-10 µm. Consequently, the height of the sample region 34 is 0.1-10 µm for filtering the suspended particles 81 greater than 10 µm in the liquid sample 8 out of the sample region 34. For example, it is adapted to separate blood cell and blood plasma for observation. The spacer 24 is disposed on the first substrate 21 or the second substrate 22 by deposition growth, etching residual, ball spraying, nano imprinting, screen printing, transfer printing, ink jet printing, etc.

The removable clamping member 26 directly or indirectly contacts the first substrate 21, the second substrate 22 or the first and second substrates 21, 22 to temporarily fix the first substrate 21, the second substrate 22 and the at least one spacer 24. In the present embodiment, the clamping member 26 comprises a first clamping portion 261 and a second clamping portion 262. The first clamping portion 261 directly contacts the surface of the first base 211 opposite to the first surface 2101. The second clamping portion 262 directly contacts the surface of the second base 221 opposite to the second surface 2201. The spacer 24 is temporarily clamped between the first substrate 21 and the second substrate 22 for providing the space of the sample region 34 whereby capillarity effect may occur.

Figure 3B:
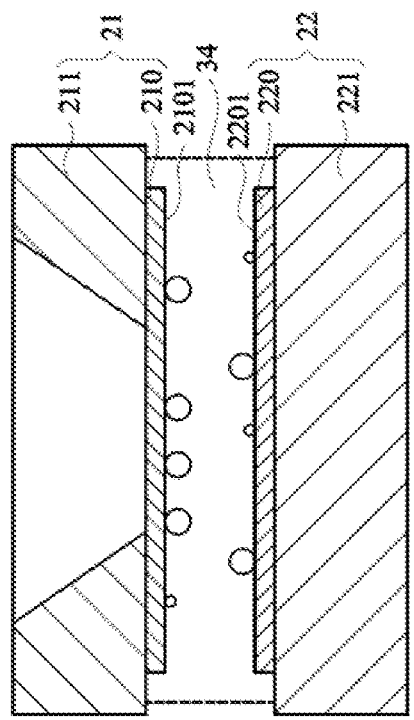
Figure 3C:
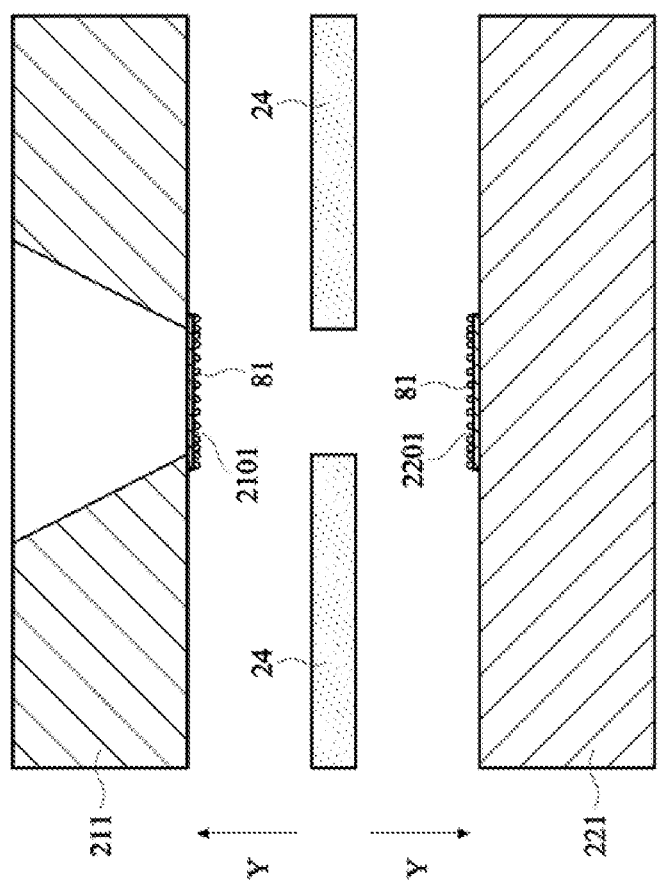

Referring to FIG. 3A to FIG. 3C, there are shown sectional schematic diagrams showing steps of a preparation method for a dried sample specimen by using the liquid sample drying apparatus of the first embodiment in accordance with the present invention. FIG. 3A and FIG. 3B are b-b' sectional views of the liquid sample drying apparatus 100 in FIG. 2A. FIG. 3C is a-a' sectional view of the liquid sample drying apparatus 100 in FIG. 2A.

As shown in FIG. 3A, the liquid sample 8 with suspended particles 81 is taken into the sample region 34 among the first substrate 21, the second substrate 22 and the spacer 24 with capillarity effect. The intake can be enhanced by air suction or pressure injection.

Figure 3D:
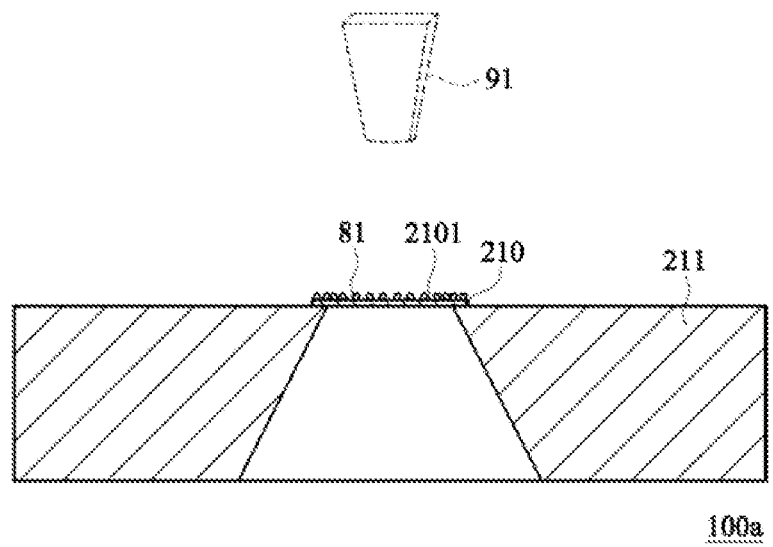
FIG. 3D is a sectional schematic diagram of a dried sample specimen in accordance with one embodiment of the present invention.
Figure 3E:
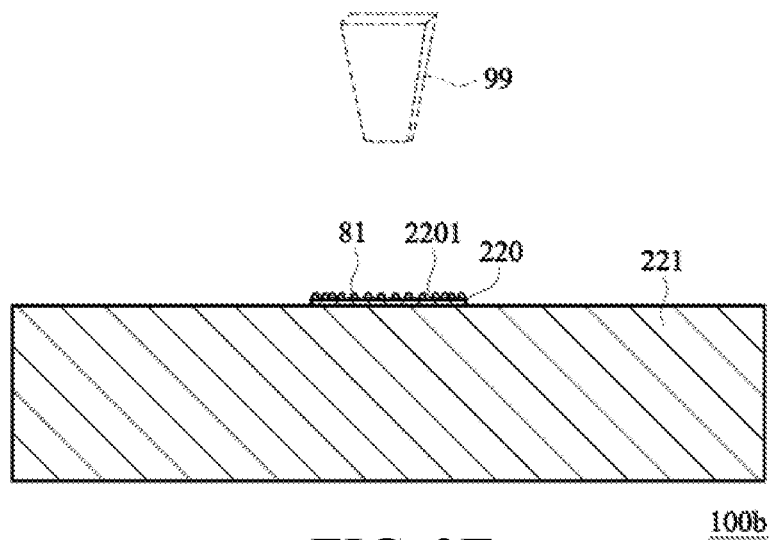
FIG. 3E is a sectional schematic diagram of a dried sample specimen in accordance with another embodiment of the present invention.

As shown in FIG. 3B, the liquid sample 8 is dried. A part of the suspended particles 81 of the liquid sample 8 are attached to the first surface 2101 of the first film 210 on the first substrate 21 and form a dried sample specimen 100a as shown in FIG. 3D. Another part of the suspended particles 81 of the liquid sample 8 are attached to the second surface 2201 of the second film 220 on the second substrate 22 and form a dried sample specimen 100b as shown in FIG. 3E. The liquid sample 8 is dried by natural evaporation, vacuum drying, low-humidity environment drying, heating drying, low-temperature drying, nitrogen environment drying or noble gas environment drying to remove component of the liquid sample 8 with high vapor pressure, such as water. The residual components attach to the first and second surfaces 2101, 2201 without flowability. The dried sample may comprise a part of liquid component, such as macromolecule component with low vapor pressure or water adsorbed, docked or clad by the residual components.

After drying, the clamping member 26 is removed and the first substrate 21, the second substrate 22 and the spacer 24 are separated as shown in FIG. 3C to form dried sample specimens 100a and 100b, as shown in FIG. 3D and FIG. 3E. The clamping member 26 is removed by, for example, cutting. The spacer 24 may be left on the first substrate 21 or the second substrate 22. The spacer 24 is non-bonding element, and may be schistic or cylindrical.

The dried sample specimen 100a comprises a part of the dried liquid sample 8 and the first substrate 21 with the first film 210, the first base 211 and the first observation window 30. The suspended particles 81 are attached to the first surface 2101 of the first film 210. The motions of the suspended particles 81 are restricted by the height h1 of the sample region 34. Consequently, the aggregation during drying is eliminated, and the distribution of the suspended particles 81 is similar to the liquid sample 8.

The first substrate 21 of the dried sample specimen 100a has small thickness and the first observation window 30 that it is adapted for observation by optical microscope, scanning electron microscope and transmission electron microscope.

Referring to FIG. 3E, the dried sample specimen 100b comprises a part of dried liquid sample 8 and the second substrate 22 with the second film 220 and the second base 221. The suspended particles 81 are attached to the second surface 2201 of the second film 220.

The dried sample specimen 100b is different from the dried sample specimen 100a by the first observation window 30. It is adapted for observation by optical microscope, scanning electron microscope and atomic force microscope 99.

Figure 4:
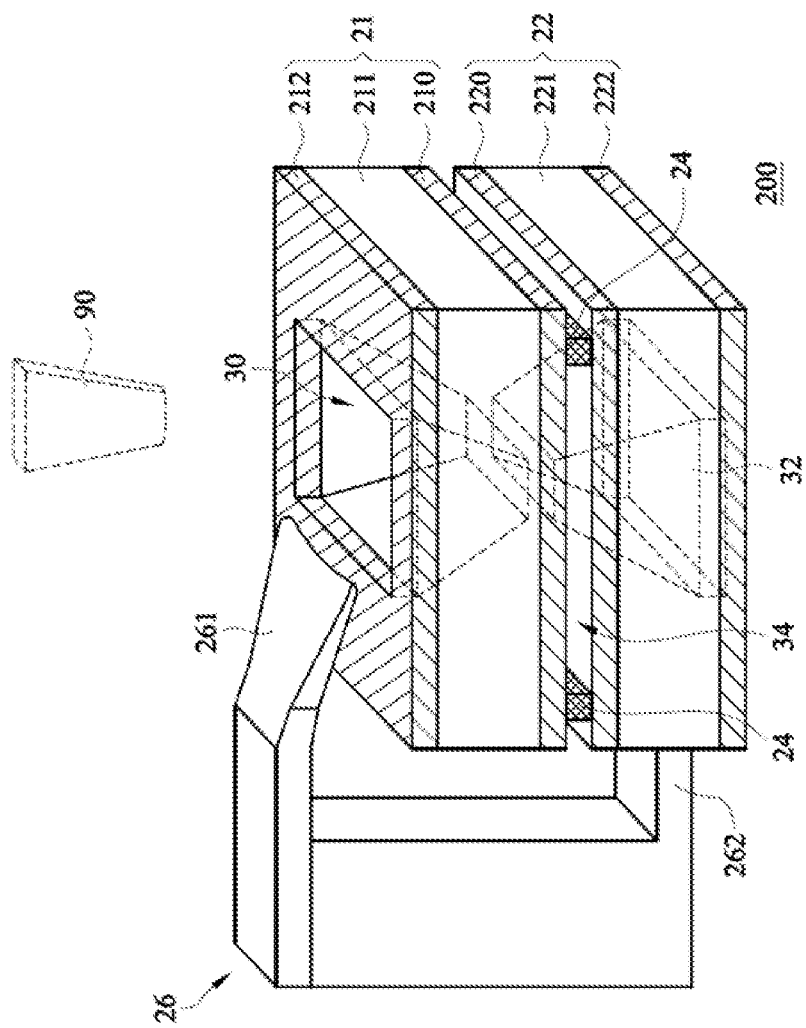
FIG. 4 is a schematic diagram of a liquid sample drying apparatus in accordance with a second embodiment of the present invention.

Referring to FIG. 4, there is shown a schematic diagram of a liquid sample drying apparatus 200 of the second embodiment in accordance with the present invention. The differences between liquid sample drying apparatus 200 and 100 are described as the following:

1. The spacers 24 are disposed between the first surface 2101 and the second surface 2201.
2. A first protection layer 212 is disposed on the surface of the first base 211 opposite to the first film 210. A second protection layer 222 is disposed on the surface of the second base 221 opposite to the second film 220. The first protection layer 212 and the second protection layer 222 are provided to prevent the first base 211 and the second base 221 from being damaged by the clamping member 26.
3. The first observation window 30 of the liquid sample drying apparatus 200 is opened through the first protection layer 212 and the first base 211 to the first film 210 by etching. Furthermore, a second observation window 32 is opened through the second protection layer 222 and the second base 221 to the second film 220 by etching. The first observation window 30 and the second observation window 32 are opposite to each other. The dried sample specimens prepared by using the liquid sample drying apparatus 200 are both adapted for observation by transmission electron microscope. Moreover, the liquid sample drying apparatus 200 with liquid sample 8 is adapted for observation by transmission electron microscope. The observation method may be the same as the method disclosed in Taiwan patent No. I330380.

Figure 5A:
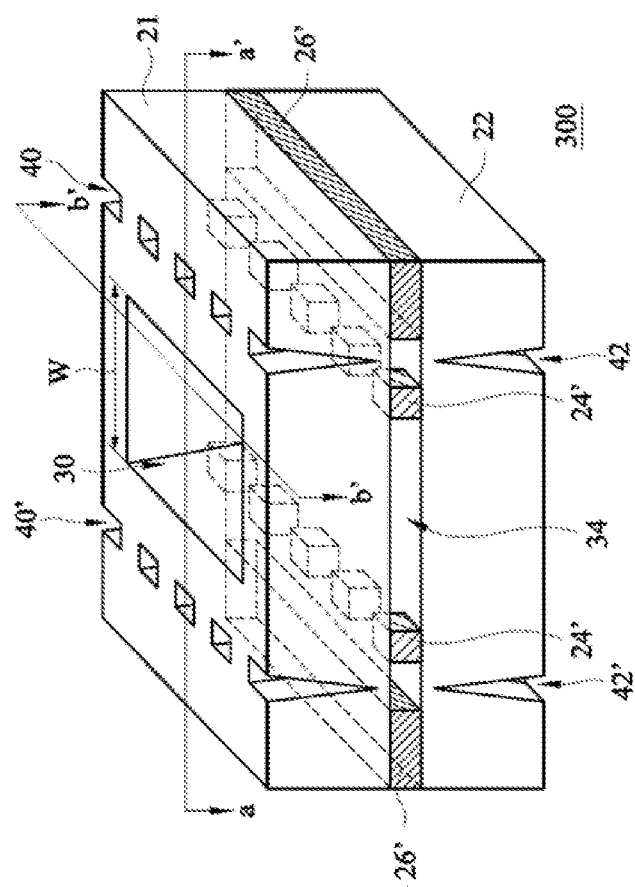
FIG. 5A is a schematic diagram of a liquid sample drying apparatus in accordance with a third embodiment of the present invention.
Figure 5B:
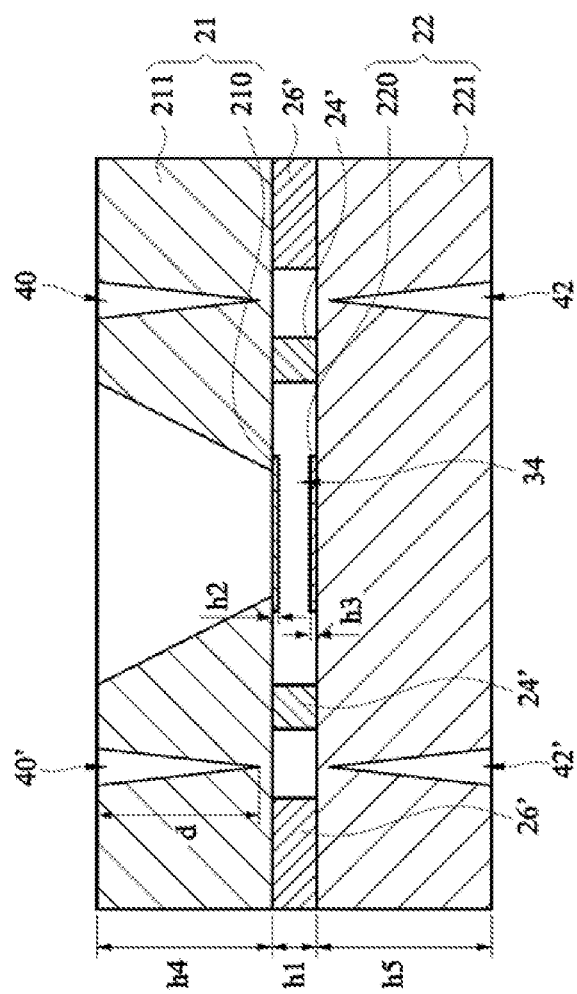
FIG. 5B is a sectional view of the liquid sample drying apparatus in accordance with the embodiment shown in FIG. 5A.

Referring to FIG. 5A and FIG. 5B, there are shown a schematic diagram and an a-a' sectional view of a liquid sample drying apparatus 300 in accordance with a third embodiment of the present invention. The liquid sample drying apparatus 300 comprises a first substrate 21, a second substrate 22, at least one spacer 24' and at least one bonding member 26'. The first substrate 21 has a first surface 2101. In particular, the first substrate 21 a first base 211 and a first film 210, wherein a first observation window 30 is disposed on the first base 211.

The second substrate 21 has a second surface 2201 facing the first surface 2101. In particular, the second substrate 22 has a second base 221 and a second film 220. The differences between liquid sample drying apparatus 300 and 100 are described as the following:

1. The liquid sample drying apparatus 300 comprises a plurality of spacers 24' with small area disposed between the first substrate 21 and the second substrate 22. The spacer 24' is the same as the spacer 24 except the shape and size. The spacers 24' in the present embodiment are open spacers 24' that the surroundings of the spacers 24' belong to the sample region 34. The spacers 24 in the first embodiment are close spacers 24 that separate the sample region 34 from the other space. When the sample region 34 is closed with air in the other space, the pressure of the liquid sample 8 can be balanced and buffered by air in the other space. In application, the opening of the sample region 34 formed by the spacers 24 can be firstly closed for microscope observation and processing (such as metal ions reduction by electron beam, or pattern writing), and then opened for the following processing or analysis, such as electrical measurement by probes or electrical connection by focused ion beam system.

2. The liquid sample drying apparatus 300 comprises at least one bonding member 26' (two bonding members 26' in the FIGS. 5A and 5B) disposed between the first substrate 21 and the second substrate 22 for fixing the first substrate 21 and the second substrate 22. The bonding member 26' is made of adhesive material, such as epoxy, UV resin, silicone, etc. In other embodiment of the present invention, anodic bonding between silicon and silicon oxide, welding or soldering between metal and alloy, bonding between metal and semiconductor, or glass frit bonding can be used for fixing the first substrate 21 and the second substrate 22. The bonding member 26' can also be distributed on the first substrate 21 or the second substrate 22 by screen printing or transfer printing.

3. The first substrate 21 comprises at least one cutting region disposed between the sample region 34 and the bonding region 26'. The cutting region 40, 40' is extended in the direction of the thickness h4, h5 of the substrate or the depth d. For example, in the liquid sample drying apparatus 300, the first cutting regions 40, 40' are disposed on the surface of the first base 211 opposite to the first film 210. The second cutting regions 42, 42' are disposed on the surface of the second base 221 opposite to the second film 220. The first cutting regions 40, 40' and the second cutting regions 42, 42' are notches provided with the same method with the first observation window 30. The depths d of the cutting regions 40, 40', 42 and 42' are less than the depth of the first or second observation window 30, 32 which can be controlled by a smaller opening for etching process.

In other embodiment of the present invention, the cutting regions can be provided with the method of laser stealth dicing cut disclosed in U.S. Pat. No. 6,992,026. In other embodiment, the cutting regions can also be provided by etching, cutter wheel cutting or laser cutting.

The bonding member 26' of a liquid sample drying apparatus with cutting region can be easily removed by breaking on the cutting region. And then, the first substrate 21 and the second substrate 22 can be easily separated to form the dried sample specimens.

Figure 6B:
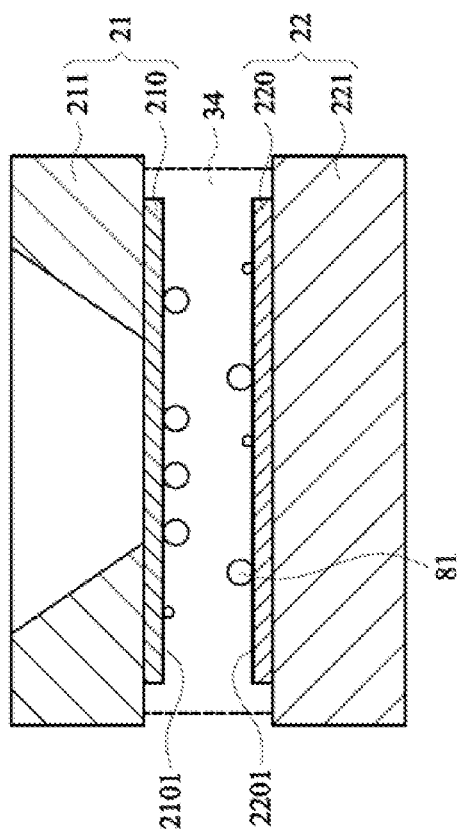
Figure 6C:
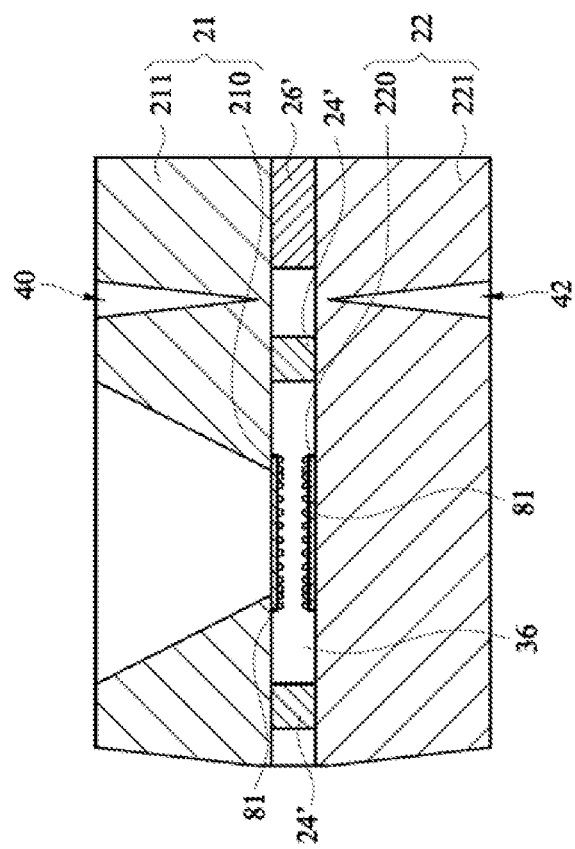

Referring to FIG. 6A to FIG. 6D, there are shown sectional schematic diagrams of the steps of a preparation method for a dried sample specimen by using the liquid sample drying apparatus of the third embodiment in accordance with the present invention. FIG. 6A and FIG. 6B are b-b' sectional views of the liquid sample drying apparatus 300 shown in FIG. 5A. FIG. 6C and FIG. 6D are a-a' sectional views of the liquid sample drying apparatus 300 shown in FIG. 5A.

As shown in FIG. 6A, the liquid sample 8 is provided and is received by the sample region 34 among the spacer 24', the first substrate 21 and the second substrate 22.

Figure 6E:
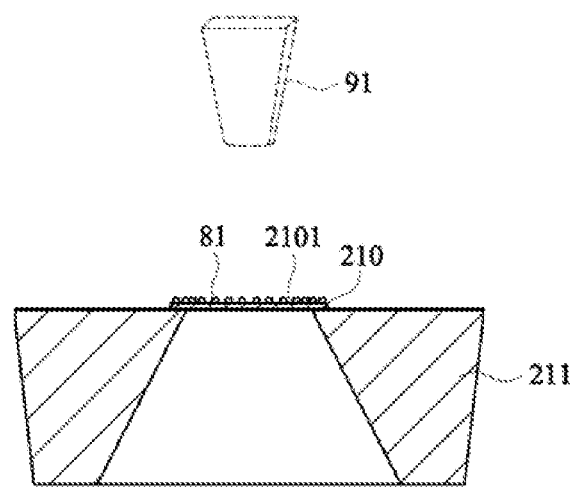
FIG. 6E is a sectional schematic diagram of a dried sample specimen in accordance with one embodiment of the present invention.

As shown in FIG. 6B, a part of the dried sample is attached to the first surface 2101 of the first substrate 21 and forms the dried sample specimen 300a as shown in FIG. 6E. The other part of the dried sample is attached to the second surface 2201 of the second substrate 22 and forms the dried sample specimen 300b as shown in FIG. 6F.

After the drying process, the first and second substrates 21, 22 are broken along the first and second cutting regions 40, 42' to remove one of the bonding members 26', as shown in FIG. 6C. The first and second substrates 21, 22 are further broken along the first and second cutting region 40, 42 to remove the other bonding member 26', as shown in FIG. 6D. And then, the dried sample specimens 300a and 300b are obtained.

In the present embodiment, the spacers 24' are disposed on the second base 221 of the second substrate 22. In the other embodiment, the spacers 24' can also be disposed on the first base 211 of the first substrate 21. In the present embodiment, the spacers 24' will be removed as shown in FIG. 6F.

Figure 6F:
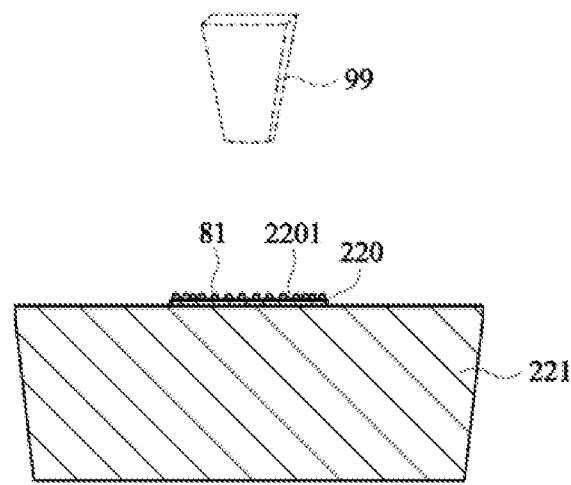
FIG. 6F is a sectional schematic diagram of a dried sample specimen in accordance with another embodiment of the present invention.

Referring to FIG. 6E and FIG. 6F, according to the abovementioned preparation method by using the liquid sample drying apparatus 300, the dried sample specimens 300a and 300b are obtained.

Referring to FIGS. 5A, 6C and 6D, in other embodiment of the present invention, the liquid sample drying apparatus 300 can be designed to have the spacer 24' and bonding member 26' in one side (such as the right side of the liquid sample drying apparatus 300 in FIGS. 5A and 6C). Consequently, the bonding member 26' can be removed by breaking the first and second substrates 21, 22 along the first and second cutting regions 40, 42 to obtain the dried sample specimens 300a and 300b as shown in FIGS. 6E and 6F.

Referring to FIGS. 5A and 5B, in another embodiment of the present invention, the liquid sample drying apparatus 300 can also be designed without cutting region. The bonding member 26' can be removed by laser or cutter wheel cutting or grinding.

Referring again to FIGS. 5A and 5B, in still another embodiment of the present invention, the liquid sample drying apparatus 300 can also be designed without spacer 24', where the bonding member 26' provides the functions of the clamping member 26 and the spacer 24'. In other words, the sample region 34 is formed among the first and second substrates 21, 22 and the bonding member 26' to receive the liquid sample 8. The height of the bonding member 26' is equal to the height h1 of the spacer 24 or 24', such that the height of the sample region 34 is 0.1-10 μm for providing capillarity. By providing the first and second cutting region, the bonding members 26' can be removed by breaking the first and second substrate 21, 22 along the first and second cutting region to obtain the dried sample specimens 300a and 300b. In the other embodiment, spacer 24' can be provided between the first and second substrate 21, 22 to prevent the first and second surface 2101, 2201 from contacting each during the removal of the bonding member 26' to protect the dried sample specimens.

Figure 7:
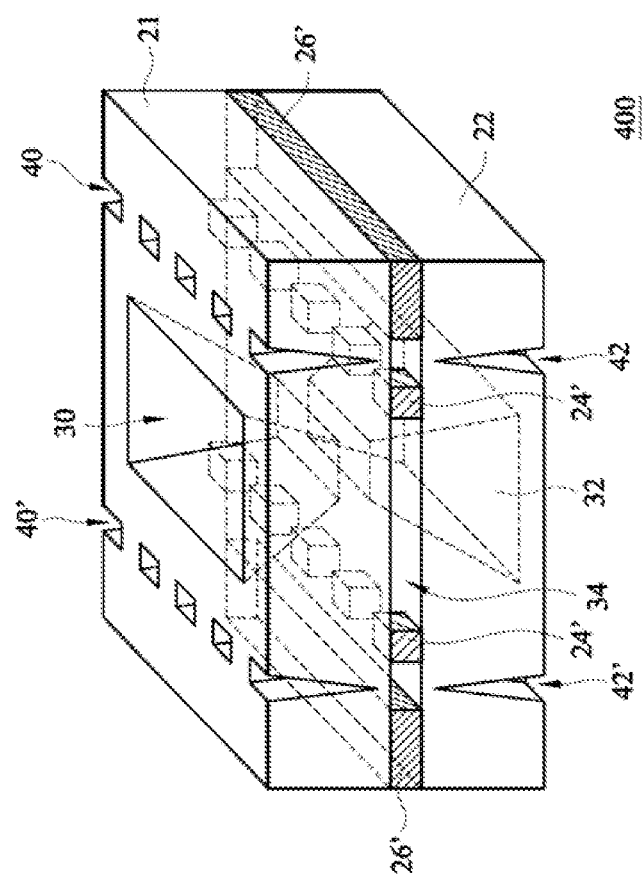
FIG. 7 is a schematic diagram of a liquid sample drying apparatus in accordance with a fourth embodiment of the present invention.

Referring to FIG. 7, there is shown a schematic diagram of a liquid sample drying apparatus in accordance with a fourth embodiment of the present invention. The liquid sample drying apparatus 400 is different from the liquid sample drying apparatus 300 by comprising a second observation window 32 on the second substrate 22. The second observation window 32 is opened through the second base 221 to the second surface 2201 and is opposite to the first observation window 30.

Figure 8A:
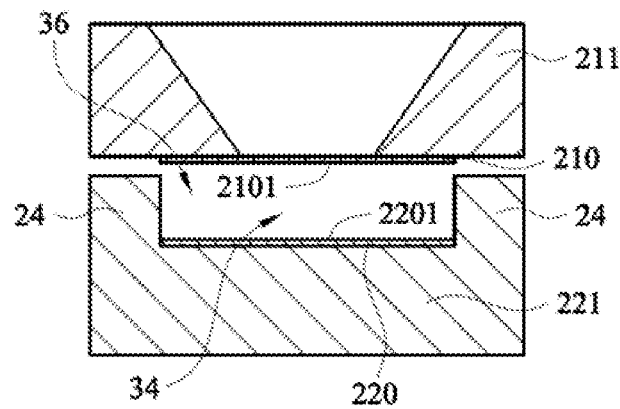
FIG. 8A to FIG. 8C are sectional schematic diagrams of spacers in accordance with a plurality of embodiments of the present invention.
Figure 8B:
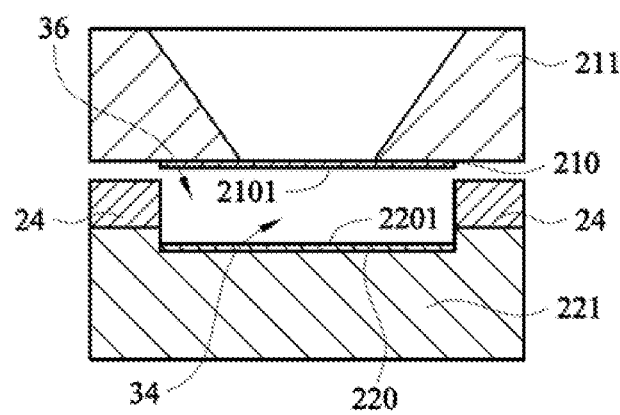
Figure 8C:
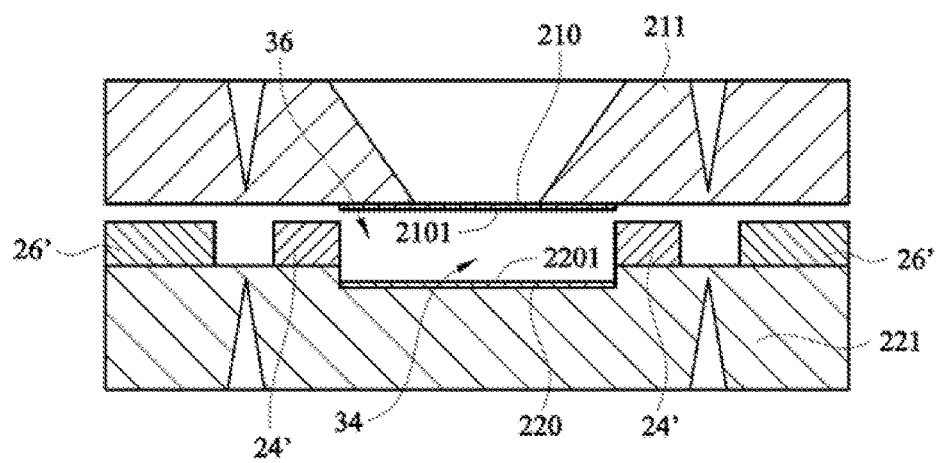

Referring to FIGS. 8A to 8C, there are shown sectional schematic diagrams of spacers in accordance with a plurality of embodiments of the present invention.

As shown in FIG. 8A, the second substrate 21 has a recess 36 disposed on the second base 221 which can be provided by etching. The second film 220 is deposited on the bottom surface of the recess 36 and forms the second surface 2201. In the other embodiment, the second surface 2201 may be the bottom surface of the recess 36. The side walls of the recess 36 are treated as the spacer 24. The sample region 34 is defined in the recess 36.

As shown in FIG. 8B, the embodiment shown in FIG. 8B is different from the embodiment shown in FIG. 8A by comprising spacers 24 disposed around the recess 36. The sample region 34 comprises the space formed by the recess 36 and the spacers 24.

Referring to FIG. 8C, the second substrate 21 has a recess 36 disposed on the second base 221. The second film 220 is deposited on the bottom surface of the recess 36. The spacers 24' and bonding members 26' are disposed beside the recess 36. The sample region 34 comprises the space formed by the recess 36, the spacers 24' and the bonding members 26'.

According to the aforementioned embodiments, the spacer 24, 24' or bonding member 26' can be provided by etching the substrate. By etching the first or second substrate 21, 22 to form the recess 36, the sample region 34 is provided. The area around the sample region 34 which is not etched can be treated as spacer 24, 24' or bonding member 26'. The spacer 24, 24' may have small area and is not bonded with the facing substrate. The bonding member 26' is bonded with the facing substrate. To bond with the facing substrate or not depends on the material or height of the surface. For example, if the surface material of the spacer 24 is silicon, it is not easy to bond with silicon substrate. If the surface material of the bonding member 26' is silicon oxide, it can be bonded to the substrate by anodic bonding. If the height of the spacer 24' is less than the height of the bonding member 26', the spacer 24' will not contact the substrate and the bonding will not be formed.

Figure 9:
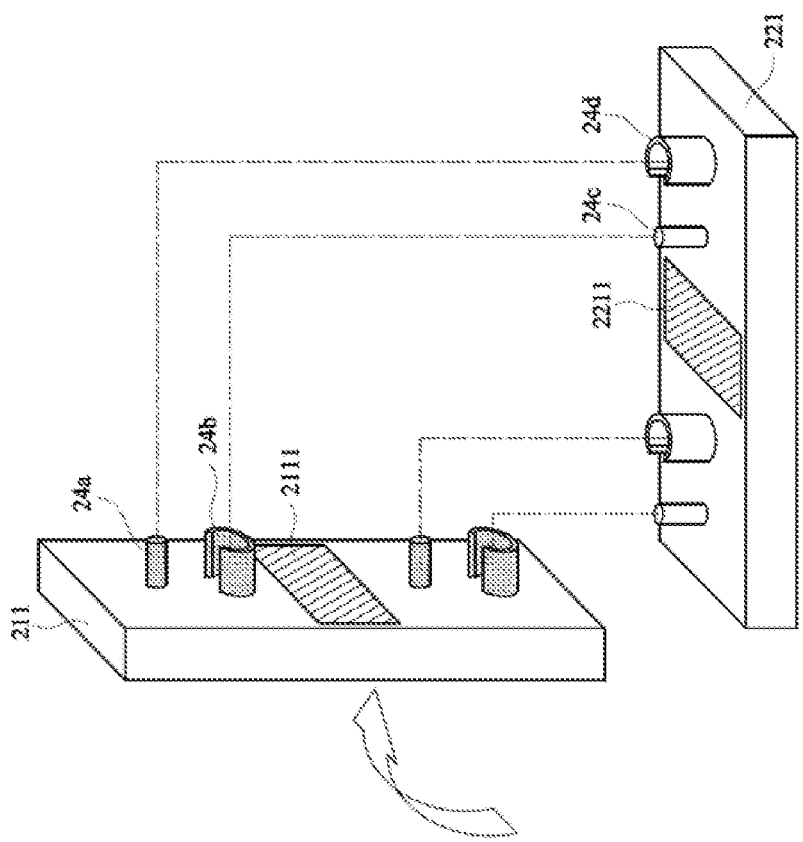
FIG. 9 is a schematic diagram of a spacer in accordance with another embodiment of the present invention.

Referring to FIG. 9, there is shown a schematic diagram of a spacer in accordance with another embodiment of the present invention. The first substrate 21 has a first surface 2111 which is a part of the surface of the first base 211. The second substrate 22 has a second surface 2211 facing the first surface 2111. The second surface 2211 is a part of the surface of the second base 221. The first and second surfaces 2111, 2211 can be modified by the same process with the first and second surfaces 2101, 2201. At least one spacer is formed on the first base 211, such as the first spacers 24a, 24b. The first spacers 24a and 24b are cylinder bump and C-shaped bump respectively. At least one spacer is formed on the second base 221, such as the second spacers 24c, 24d. The second spacers 24c and 24d are cylinder bump and C-shaped bump respectively. When the first and second substrates 21, 22 are assembled, the first and second surfaces 2111, 2211 are substantially parallel and the first spacers 24a and 24b are coupled to the second spacers 24c and 24d respectively. The coupling of the first spacers 24a, 24b and the second spacers 24c, 24d restricts the relative movement between the first and the second substrates 21, 22.

Figure 10:
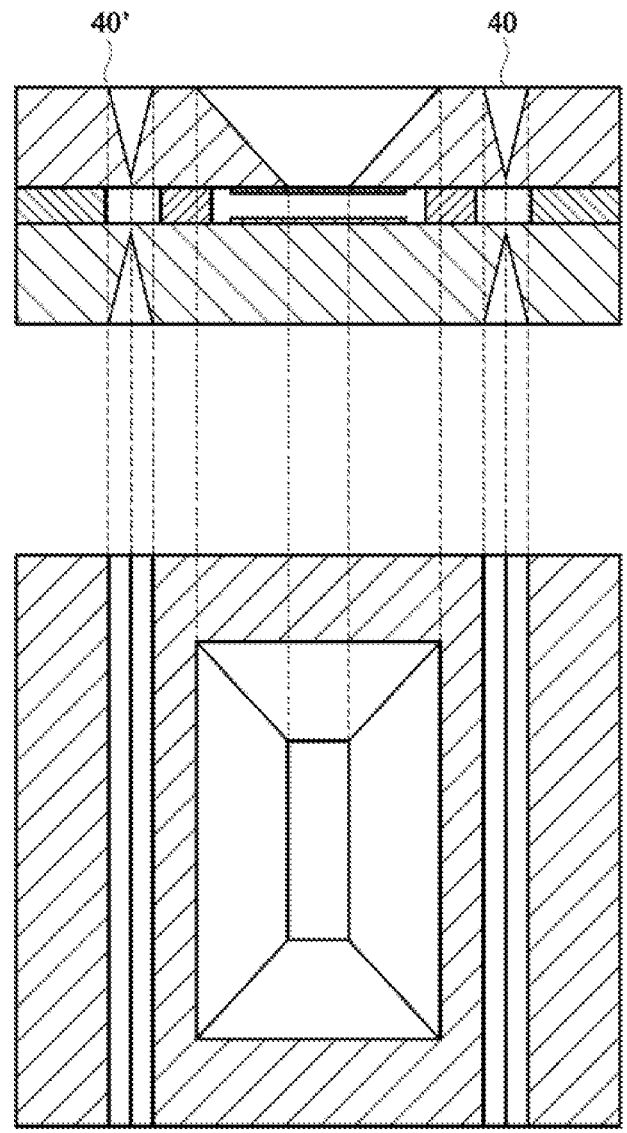
FIG. 10 shows a top view and a side view of cutting regions in accordance with one embodiment of the present invention.

Referring to FIG. 10, there are shown a top view and a side view of cutting regions in accordance with one embodiment of the present invention. The first and second cutting regions 40, 40' can be provided by laser cutting, cutter wheel cutting or laser stealth dicing cutting to form grooves.

Figure 11:
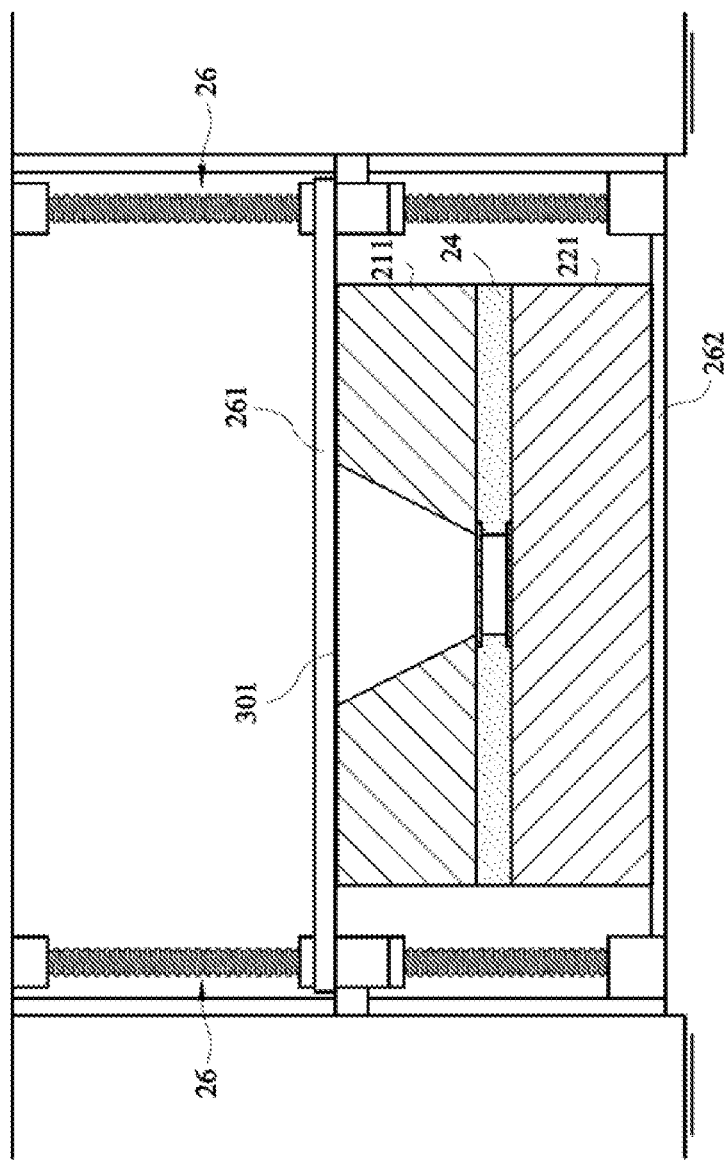
FIG. 11 is sectional schematic diagram of a clamping member in accordance with another embodiment of the present invention.

Referring to FIG. 11, there is shown a sectional schematic diagram of a clamping member in accordance with another embodiment of the present invention. The clamping member 26 of the present embodiment comprises a first clamping portion 261 and a second clamping portion 262. Both the first and second clamping portions 261, 262 are platform structure. By clamping the first and second bases 211, 221 with the first and second clamping portions 261, 262 respectively, the first substrate 21, the second substrate 22 and the spacers 24 are temporarily fixed.

By using the liquid sample drying apparatus, dried sample specimen and preparation method of the present invention, the liquid sample drying apparatus and the dried sample specimens are adapted for the observation of optical microscope, atomic force microscope, transmission electron microscope, scanning electron microscope, etc.

The above disclosure is only the preferred embodiment of the present invention, and not used for limiting the scope of the present invention. All equivalent variations and modifications on the basis of shapes, structures, and features described in claims of the present invention should be included in the scope of the present invention.

INDUSTRIAL APPLICABILITY

By using the liquid sample drying apparatus and the preparation method by using the liquid sample drying apparatus of the present invention, the spacers or bonding members provide a height for the sample region to receive the liquid sample with capillarity effect. Since the height between the first and second substrate is provided by the spacers or bonding members, the liquid sample between the first and second substrates has substantially uniform thickness that restricts the flow of the liquid sample during drying. Consequently, the aggregation of the suspended particles during drying is eliminated.

The spacers are only disposed between the first and second substrates and are not going to bond with the first and second substrates. Once the clamping member or bonding member is removed after drying, the first and second substrates with dried sample can be separated to form the dried sample specimens.

Furthermore, the bonding and non-bonding properties of the elements are relative description. Since the van der Waals' force is the nature of objects under nanometer proximity, if the objects are close enough to each other, they are attractive to each other. Consequently, the definition of "non-bonding" in the present invention is that when the objects are separated, the structure of the objects won't be damaged. Moreover, the sample drying apparatus is configured to be easy to be opened to form sample specimen with the dried sample exposed. The sample specimen of the present invention is adapted for a plurality types of microscopes and analysis methods, such as an electron microscope, an atomic force microscope, Matrix-Assisted Laser Desorption/Ionization Time of Flight Mass Spectrometry (MALDI-TOF-MS), probe contact electrical analysis, etc.

What is claimed is:

1. A liquid sample drying apparatus, comprising:
   two substrates, wherein each of the two substrates has a surface respectively and the two surfaces face each other; and
   at least one bonding member disposed between and bonding with the two substrates so as to form a sample region between the two surfaces to receive a liquid sample; wherein the substrates comprise at least one cutting region extending in a direction of a thickness of the substrates and disposed between the sample region and the bonding member.

2. The apparatus as claimed in claim 1, further comprising at least one spacer disposed between the two substrates, wherein the at least one spacer and the sample region are on the same side of the at least one cutting region.

3. The apparatus as claimed in claim 2, wherein the at least one spacer is fixed on one of the two substrates.

4. The apparatus as claimed in claim 1, wherein a recess is disposed on one of the two substrates; one of the two surfaces is the bottom surface of the recess; the spacer is a side wall of the recess; and the sample region is in the recess.

5. The apparatus as claimed in claim 1, an observation window is disposed on one of the two substrates.

6. The apparatus as claimed in claim 1, wherein the sample region has a height between 0.1 µm and 10 µm.

7. A liquid sample drying apparatus, comprising:
   two substrates, wherein each of the two substrates has a surface respectively and the two surfaces face each other;
   at least one bonding member disposed between and bonding with the two substrates so as to form a sample region between the two surfaces to receive a liquid sample; wherein the substrates comprise at least one cutting region extending in a direction of a thickness of the substrates and disposed between the sample region and the bonding member; and
   at least one spacer disposed between the two substrates.

8. The apparatus as claimed in claim 7, wherein the at least one spacer and the sample region are on the same side of the at least one bonding member.

9. The apparatus as claimed in claim 7, wherein a recess is disposed on one of the two substrates; one of the two surfaces is the bottom surface of the recess; the spacer is a side wall of the recess; and the sample region is in the recess.

10. The apparatus as claimed in claim 7, wherein the at least one spacer is fixed on one of the two substrates.

11. The apparatus as claimed in claim 7, wherein the sample region has a height between 0.1 µm and 10 µm.

12. The apparatus as claimed in claim 7, wherein an observation window is disposed on one of the two substrates.

13. A preparation method for a dried sample specimen, comprising:

providing the liquid sample drying apparatus as claimed in claim 1;

receiving a liquid sample to the sample region;

drying the liquid sample, wherein a part of the dried liquid sample is attached to the surface of one of the two substrates and forms a dried sample specimen; and breaking the substrates along the cutting region to remove the bonding member and separate the dried sample specimen.

14. The preparation method as claimed in claim 13, wherein the method of drying the liquid sample is selectively one of natural evaporation, vacuum drying, low-humidity environment drying, heating drying, low-temperature drying, nitrogen environment drying, noble gas environment drying or the combination thereof.

15. A dried sample specimen prepared by the preparation method claimed in claim 13, comprising: the part of the dried liquid sample and the one substrate, wherein the part of the dried liquid sample is attached to the surface of the one substrate.

16. A preparation method for a dried sample specimen, comprising:

providing the liquid sample drying apparatus as claimed in claim 7;

receiving a liquid sample to the sample region;

drying the liquid sample, wherein a part of the dried liquid sample is attached to the surface of one of the two substrates and forms a dried sample specimen; and removing the at least one bonding member to separate the dried sample specimen.

17. The preparation method as claimed in claim 16, wherein the method of drying the liquid sample is selectively one of natural evaporation, vacuum drying, low-humidity environment drying, heating drying, low-temperature drying, nitrogen environment drying, noble gas environment drying or the combination thereof.

18. The preparation method as claimed in claim 16, wherein the method of removing the at least one bonding member is selectively one of pressure applying, laser cutting, cutter wheel cutting, grinding, laser stealth dicing cutting or the combination thereof.

19. A dried sample specimen prepared by the preparation method claimed in claim 16, comprising: the part of the dried liquid sample and the one substrate, wherein the part of the dried liquid sample is attached to the surface of the one substrate.

* * * * *